(12) United States Patent
Anderson-Cunanan et al.

(10) Patent No.: US 10,443,107 B2
(45) Date of Patent: Oct. 15, 2019

(54) TISSUE MODIFICATION DEVICES, SYSTEMS, AND METHODS

(71) Applicant: Boston Scientific Scimed, Inc., Maple Grove, MN (US)

(72) Inventors: Crystal Marie Anderson-Cunanan, San Jose, CA (US); Daniel J. Foster, Lino Lakes, MN (US); Ray McCarthy, Galway (IE); Mary M. Byron, Roseville, MN (US); David Robert Wulfman, Minneapolis, MN (US); Bradley S. Swehla, Eagan, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/044,845

(22) Filed: Jul. 25, 2018

(65) Prior Publication Data
US 2018/0327871 A1 Nov. 15, 2018

Related U.S. Application Data

(63) Continuation of application No. 15/250,382, filed on Aug. 29, 2016, now Pat. No. 10,080,820.
(Continued)

(51) Int. Cl.
*G01N 1/00* (2006.01)
*C14B 1/00* (2006.01)
(Continued)

(52) U.S. Cl.
CPC ............. *C14B 1/00* (2013.01); *A61F 2/2415* (2013.01); *A61L 27/3625* (2013.01);
(Continued)

(58) Field of Classification Search
CPC ........................................................ G01N 1/00
See application file for complete search history.

(56) References Cited

U.S. PATENT DOCUMENTS 1,911,556 A 5/1933 Destaebler
1,919,649 A 7/1933 Griffin et al.
(Continued)

FOREIGN PATENT DOCUMENTS

CN 201040047 3/2008
CN 201161003 12/2008
(Continued)

OTHER PUBLICATIONS

Ferrans, Victor J. et al., "Calcific Deposits in Porcine Bioprostheses: Structure and Pathogenesis," The American Journal of Cardiology, Nov. 1980 46:5 (721-734) (14 pages).
File History for European Patent Application No. 15747312.5 downloaded Sep. 14, 2018 (180 pages).
(Continued)

*Primary Examiner* — Jyoti Nagpaul
(74) *Attorney, Agent, or Firm* — Pauly, DeVries Smith & Deffner LLC

(57) ABSTRACT

A tissue modification apparatus includes at least a first plurality of grippers aligned in a plane adapted to secure a first edge of a patch of tissue. The plurality of grippers are each secured to a first force actuator. The first plurality of grippers are each adapted to pivot relative to the first force actuator about an axis perpendicular to the plane. In some cases, a plurality of grippers are attached to a force actuator by a passive force transfer mechanism. In some cases, individual force actuators are attached by pivoted connections to individual grippers. Methods of treating tissue can secure tensioned tissue to a frame to retain the tension during a treatment (e.g., cross-linking the tissue with a chemical cross-linker).

11 Claims, 8 Drawing Sheets

Related U.S. Application Data

(60) Provisional application No. 62/213,868, filed on Sep. 3, 2015.

(51) Int. Cl.
*A61F 2/24* (2006.01)
*C14B 1/26* (2006.01)
*C14B 17/08* (2006.01)
*A61L 27/36* (2006.01)
*D02J 1/22* (2006.01)

(52) U.S. Cl.
CPC ....... *A61L 27/3687* (2013.01); *A61L 27/3691* (2013.01); *C14B 1/26* (2013.01); *C14B 17/08* (2013.01); *A61L 2430/20* (2013.01); *A61L 2430/40* (2013.01); *D02J 1/227* (2013.01)

(56) References Cited

U.S. PATENT DOCUMENTS

| | | | |
|---|---|---|---|
| 2,185,441 | A | 1/1940 | Jureczki |
| 2,494,949 | A | 1/1950 | Langdahl |
| 2,594,902 | A | 4/1952 | Frazier |
| 2,704,415 | A | 3/1955 | Shiffman |
| 4,681,588 | A | 7/1987 | Ketharanathan |
| 4,800,603 | A | 1/1989 | Jaffe et al. |
| 4,811,576 | A | 3/1989 | Davis |
| 5,298,012 | A | 3/1994 | Handlos et al. |
| 5,876,325 | A * | 3/1999 | Mizuno .............. A61B 1/00048 600/102 |
| 5,902,228 | A | 5/1999 | Schulsinger et al. |
| 6,093,530 | A | 7/2000 | McIlroy et al. |
| 6,796,977 | B2 | 9/2004 | Yap et al. |
| 7,622,276 | B2 | 11/2009 | Cunanan et al. |
| 8,137,411 | B2 | 3/2012 | Schankereli et al. |
| 8,834,349 | B2 | 9/2014 | Gregg et al. |
| 8,846,390 | B2 | 9/2014 | Dove et al. |
| 9,056,007 | B2 | 6/2015 | Waisblatt et al. |
| 9,408,687 | B2 | 8/2016 | Waisblatt et al. |
| 10,080,820 | B2 | 9/2018 | Anderson-Cunanan et al. |
| 2002/0038478 | A1 | 4/2002 | Crossley |
| 2005/0096502 | A1* | 5/2005 | Khalili .................. A61B 1/018 600/106 |
| 2005/0143809 | A1 | 6/2005 | Salahieh et al. |
| 2005/0229323 | A1 | 10/2005 | Mills et al. |
| 2009/0069880 | A1 | 3/2009 | Vonderwalde et al. |
| 2013/0012767 | A1 | 1/2013 | Nguyen et al. |
| 2013/0079891 | A1 | 3/2013 | Waisblatt et al. |
| 2014/0379095 | A1 | 12/2014 | Waisblatt et al. |
| 2015/0272717 | A1 | 10/2015 | Waisblatt et al. |
| 2016/0022254 | A1 | 1/2016 | Mccarthy |
| 2017/0065744 | A1 | 3/2017 | Anderson-Cunanan et al. |

FOREIGN PATENT DOCUMENTS

| | | |
|---|---|---|
| CN | 101721745 | 6/2010 |
| CN | 107072653 | 8/2017 |
| DE | 181235 | 2/1907 |
| EP | 3171903 | 5/2017 |
| EP | 3344786 | 7/2018 |
| JP | 2017521184 | 8/2017 |
| WO | 9606192 | 2/1996 |
| WO | 2016014533 | 1/2016 |
| WO | 2017040756 | 3/2017 |

OTHER PUBLICATIONS

File History for U.S. Appl. No. 14/804,956 downloaded Sep. 13, 2018 (285 pages).
File History for U.S. Appl. No. 13/626,578 downloaded Sep. 13, 2018 (126 pages).
File History for U.S. Appl. No. 14/481,477 downloaded Sep. 13, 2018 (138 pages).
File History for U.S. Appl. No. 14/739,909 downloaded Sep. 13, 2018 (188 pages).
File History for European Patent Application No. 16766168.5 downloaded Sep. 14, 2018 (225 pages).
File History for U.S. Appl. No. 15/250,382 downloaded Sep. 13, 2018 (285 pages).
Fishbein, et al., "Calcifications of Cardiac Valve Bioprostheses. Biochemical, histologic, and ultrastructural observations in a subcutaneous implantation model system," J Thorac Cardiovasc Surg 1982, 83: 602-9 (8 pages).
"International Preliminary Report on Patentability," for PCT Application No. PCT/US2015/041334 dated Feb. 2, 2017 (11 pages).
"International Preliminary Report on Patentability," for PCT Application No. PCT/US2016/049851 dated Mar. 15, 2018 (11 pages).
"International Search Report and Written Opinion," for PCT Application No. PCT/US2015/041334, dated Feb. 8, 2015 (17 pages).
"International Search Report and Written Opinion," for PCT Application No. PCT/US2016/049851 dated Jan. 30, 2017 (16 pages).
"Invitation to Pay Additional Fees," in International Patent Application No. PCT/US2015/041334, dated Nov. 11, 2015 (5 pages).
Langdon, S. E. et al., "Biaxial mechanical/structural effects of equibiaxial strain during crosslinking of bovine pericardial xenograft materials," Biomaterials, vol. 20, Issue 2, Jan. 1999, (pp. 137-153).
"Partial International Search Report," for PCT/US2016/049851 dated Dec. 1, 2016 (6 pages).
Schoen, et al., "Calcification of Bovine Pericardium used in Cardiac Valve Bioprostheses. Implications for the Mechanisms of Bioprosthetic Tissue Mineralization," American Journal of Pathology 1986, 123: 134-45 (12 pages).
Schoen, Frederick J. et al., "Onset and Progression of Experimental Bioprosthetic Heart Valve Calcification," Laboratory Investigation, 1985 vol. 52, No. 5, p. 523-532 (8 pages).
Zioupos, P. et al., "Anisotropic Elasticity and Strength of Gluaraldehyde Fixed Bovine Pericardium for use in Pericardial Bioprosthetic Valves," J. Biomedical Materials Res, 1994, 28:49-57 (10 pages).
Communication Pursuant to Article 94(3) EPC for European Patent Application No. 16766168.5 dated Dec. 11, 2018 (3 pages).
First Office Action for Chinese Patent Application No. 201580050938.7 dated Nov. 26, 2018 (12 pages) with English Translation.
Office Action for Japanese Patent Application No. 2017-503548 dated Mar. 5, 2019 (3 pages) No English Translation.
Response to Final Rejection dated Nov. 6, 2018, for U.S. Appl. No. 14/804,956, submitted via EFS-Web on Feb. 6, 2019, 8 pages.
Final Office Action for U.S. Appl. No. 14/804,956 dated Nov. 6, 2018 (15 pages).
Office Action for Japanese Patent Application No. 2017-503548 dated Nov. 27, 2017 (4 pages) 7 pages, with English translation.
Response to Communication Pursuant to Rules 161(1) and 162 EPC for European Patent Application No. 16766168.5 filed with the EPO on Oct. 11, 2018 (6 pages).
Communication Pursuant to Rule 164(2)(b) and Article 94(3) EPC for European Patent Application No. 16766168.5 (our file 115.0251EPWO) dated May 23, 2019 (7 pages).

\* cited by examiner

TISSUE MODIFICATION DEVICES, SYSTEMS, AND METHODS

This application is a continuation application of U.S. application Ser. No. 15/250,382, filed Aug. 29, 2016, which claims the benefit of U.S. Provisional Application No. 62/213,868, filed Sep. 3, 2015, the contents of all of which are herein incorporated by reference.

TECHNICAL FIELD

The following disclosure relates to tissue modification devices, systems, and methods and, more particularly, to modification of biological tissue for implantation in a mammal.

BACKGROUND

Heart valve surgery can be used to repair or replace diseased heart valves. For example, heart valve replacement may be indicated when there is a narrowing of the native heart valve, commonly referred to as stenosis, or when the native valve leaks or regurgitates. The repair or replacement of diseased heart valves can include, for example, the introduction of a prosthetic heart valve that includes biological tissue heterologous to the patient (e.g., a heterograft or xenograft).

Biological tissue can have mechanical properties that vary within a single donor and/or from among several donors of the same species. For example, biological tissue from a single donor can have non-uniform thickness, and the average thickness of biological tissue can vary from one donor to another. The variation in mechanical properties of biological tissue used in replacement heart valves can impact the performance and/or durability of a replacement heart valve implanted in a patient.

SUMMARY

Tissue modification changes one or more mechanical properties of biological tissue used for implantation in a mammal. In some cases, tissue modification devices provided herein can stretch a patch of biological tissue such that an equal amount of tension is supplied to different sections of the biological tissue even if the biological tissue has inconsistent elastic properties.

In Example 1, a tissue modification apparatus can include at least a first plurality of grippers aligned in a plane adapted to secure a first edge of a patch of tissue. The plurality of grippers are each secured to a first force actuator. The first plurality of grippers are each adapted to pivot relative to the first force actuator about an axis perpendicular to the plane.

In Example 2, the tissue modification apparatus of Example 1 further including a second plurality of grippers aligned in the plane opposite the first plurality of grippers, the second plurality of grippers being adapted to secure a second edge of a patch of tissue. The second plurality of grippers are each adapted to pivot about an axis perpendicular to the plane. The first plurality of grippers being adapted to pull the tissue in a direction opposite the second plurality of grippers such that a patch of tissue secured between the first and second plurality of grippers can be stretched along a first orientation.

In Example 3, the tissue modification apparatus of Example 2 has the second plurality of grippers each being secured to a second force actuator such that the first and second force actuators are adapted to pull the first and second pluralities of grippers in opposite directions such that a patch of tissue secured between the first and second plurality of grippers can be stretched along a first orientation.

In Example 3, the tissue modification apparatus of Example 2 has the second plurality of grippers attached to a stationary object.

In Example 4, the tissue modification apparatus of Example 3 or Example 4 where the plurality of grippers are each adapted to pivot relative to the second force actuator of Example 2 or the stationary object of Example 3 about an axis perpendicular to the plane.

In Example 5, the tissue modification apparatus of one of Examples 1-5 further includes a third plurality of grippers and a fourth plurality of grippers. The third plurality of grippers is aligned in the plane adjacent the first plurality of grippers and the fourth plurality of grippers is aligned in the plane opposite the third plurality of grippers. The third and fourth pluralities of grippers are each adapted to secure a third and fourth edge of a patch of tissue. At least the third plurality of grippers are each secured to a third force actuator. The third plurality of grippers are each adapted to pivot relative to the third force actuator about an axis perpendicular to the plane. The fourth plurality of grippers are either secured to a fourth force actuator or a stationary object and each is adapted to pivot relative to the fourth force actuator or the stationary object about an axis perpendicular to the plane. The third force actuator is adapted to pull the third plurality of grippers in a direction opposite the fourth plurality of grippers such that a patch of tissue secured between the first, second, third, and fourth plurality of grippers can be stretched along both the first orientation and a second orientation.

In Example 6, the tissue modification apparatus of Example 5 includes a fourth force actuator and the third and fourth force actuators are adapted to pull the third and fourth pluralities of grippers in opposite directions.

In Example 7, the tissue modification apparatus of Example 5 includes a stationary object that the forth plurality of grippers are secured to by a plurality of pivoted connections.

In Example 8, the tissue modification apparatus of one of Examples 1-7 wherein each of the grippers is secured to a distal end of a beam, each beam being pivotally connected to a force divider.

In Example 9, the tissue modification apparatus of Example 8 wherein each force divider is pivotally connected to either another force divider or to one of said force actuators and each force divider includes at least three pivoted connections.

In Example 10, the tissue modification apparatus of one of Examples 8 or 9 further including a beam fixation device adapted to lock grippers in one of said pluralities of grippers into a predetermined spacing. The beam fixation device is adapted to be released to allow for the grippers to pivot after being secured to an edge of tissue.

In Example 11, the tissue modification apparatus of one of Examples 8-10 wherein each beam is at least 1 cm long, more preferably at least 2 cm long.

In Example 12, a tissue modification apparatus comprises a plurality of grippers adapted to be secured around a periphery of a patch of tissue and a plurality of force actuators attached to the plurality of grippers such that adjacent grippers are adapted to supply an equal tension to the patch of tissue regardless of differences in the elastic properties of different portions of the patch of tissue.

In Example 13, the tissue modification apparatus of Example 12, wherein each force actuator is connected to a single gripper.

In Example 14, the tissue modification apparatus of Example 13, wherein each force actuator is connected to a single gripper via a pivoted connection adapted to allow the gripper to pivot relative to the force actuator in the plane of the patch of tissue.

In Example 15, the tissue modification apparatus of one of Examples 12-14, wherein the actuators are adapted to provide a force such that each gripper supplies an equal tension to the tissue.

In Example 16, a method for treating tissue includes (a) attaching a patch of tissue to a plurality of grippers around the periphery of the patch; (b) applying a force to at least some of the grippers to apply tension to the patch of tissue; (c) securing the patch while under tension to a frame so that the tissue retains the tension; and (d) contacting the patch of tissue with a cross-linking chemical while secured to the frame and under tension to cross-link the patch while under tension.

In Example 17, the method of Example 16 wherein each of the grippers along each side of the patch applies an equal amount of force.

In Example 18, the method of one of Example 17, wherein a passive force transfer mechanism is used to equalize force along each side of the patch.

In Example 19, the method of one of Examples 16-18 wherein each gripper applies an equal amount of stretching force.

In Example 20, the method of one of Examples 16-19 wherein the patch is approximately rectangular in shape and grippers are attached along four sides of the patch such that each side is attached to a number of grippers equal to 2n, where n is equal to an integer of 1 or greater, preferably an integer of 2 or greater.

In Example 21, the method of one of Examples 16-20, wherein the chemical is glutaraldehyde.

In Example 22, the method of one of Examples 16-21, further comprising cutting a leaflet out of the patch of tissue.

In Example 23, the method of one of Examples 16-22, wherein the patch of tissue comprises pericardium. In some embodiments, the piece of tissue is exposed to a glutaraldehyde solution. Additionally or alternatively, the piece of tissue can be exposed to the glutaraldehyde solution during at least a portion of the exposure of the piece of tissue to the first and second stress loads. For example, the piece of tissue can be exposed to the glutaraldehyde solution for between about 15 minutes to about two weeks while under stress loads due to attachment to a frame.

In certain embodiments, the substantially planar patch of pericardial tissue is bovine pericardium, equine pericardium, or porcine pericardium.

In another aspect, a tissue modification method includes forming a substantially planar leaflet from a piece of pericardial tissue, arranging the substantially planar leaflet in a stationary position relative to a base, and removing tissue from at least a portion of a substantially planar surface of the substantially planar leaflet. The substantially planar leaflet includes a coaptation portion, an arcuate edge substantially opposite the coaptation portion, the arcuate edge having a first end and a second end, and a belly extending from the arcuate edge to an axis defined by the first end and second ends of the arcuate edge.

The details of one or more embodiments of the invention are set forth in the accompanying drawings and the description below. Other aspects, features, and advantages of the invention will be apparent from the description and drawings, and from the claims.

DESCRIPTION OF DRAWINGS

Like reference symbols in the various drawings indicate like elements.

DETAILED DESCRIPTION

Prosthetic heart valves and other implantable medical devices often use biological tissues in order to obtain the desired biological and mechanical properties. Because the variation in mechanical properties of biological tissue used in replacement heart valves can impact the performance and/or durability of a medical device, methods, devices, and systems provided herein provide more reliable and consistent mechanical properties for biological tissues.

Figure 1:
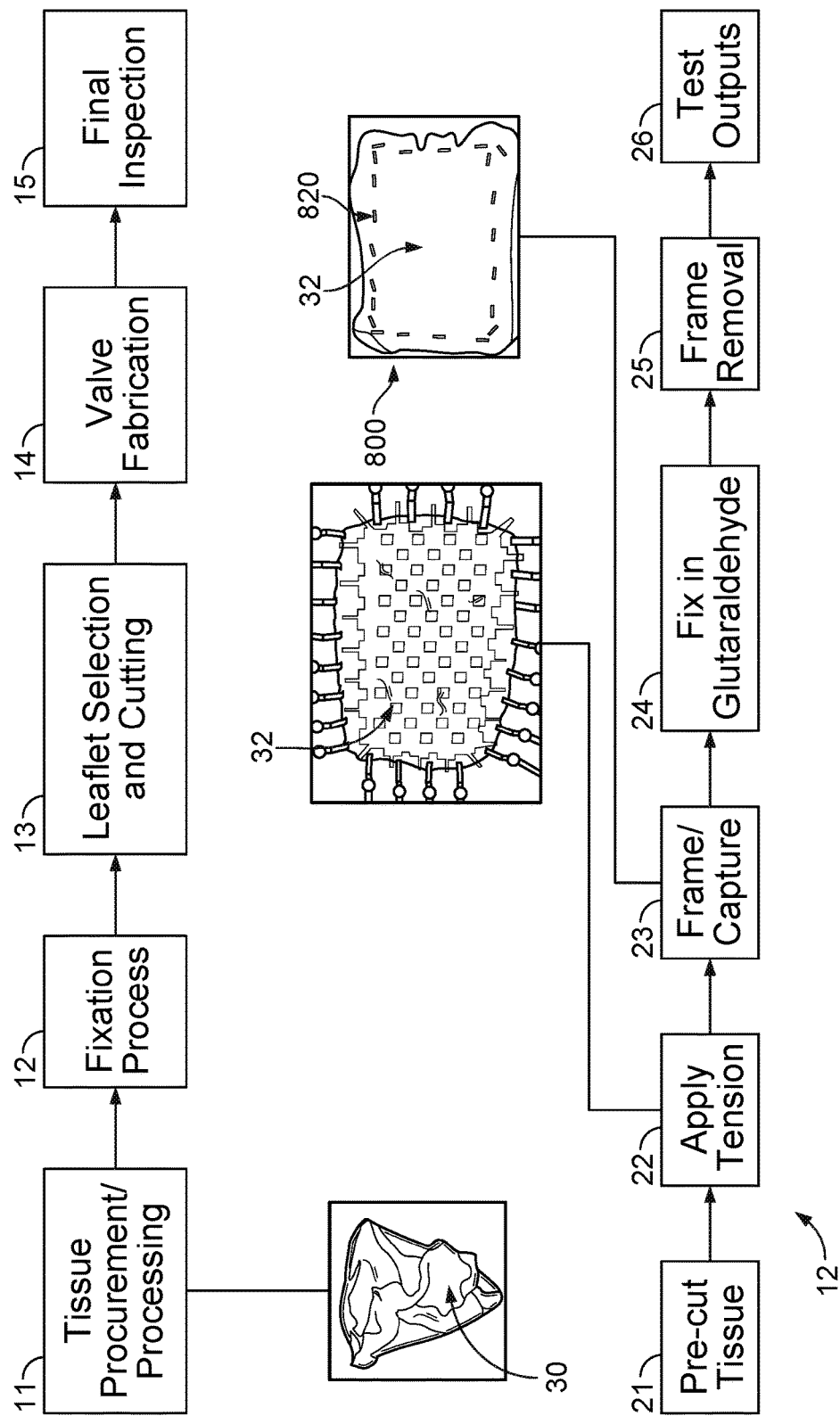
FIG. 1A is flow chart depicting an exemplary method for producing a heart valve using biological tissues.
FIG. 1B is a flow chart depicting a method of treating tissue according to some embodiments of the methods provided herein.

FIG. 1A is a flow chart depicting the overall process of incorporating biological tissue into a prosthetic heart valve. The first step 11 is to procure a biological tissue for use in a prosthetic heart valve, such as bovine pericardium 30. In some cases, porcine pericardium or equine pericardium can be obtained. In some cases, other animal or human biological tissues can be obtained and used in processes described herein. In some cases, animal biological tissues can be obtained from organizations that are certified by one or more government or non-government organizations as providing biological tissues suitable for use in medicines or medical devices and/or that the animals have been raised according to particular regulations, which can reduce the risk of transmitting agents of animal spongiform encephalopathies. In some cases, animal tissues can be pretreated by a supplier. For example, the supplier might pre-clean the tissue, which can include removing adhering fat and/or rinsing away blood and debris. A supplier might also rinse the tissue with one or more antimicrobial solutions or have specific tonicity requirements.

Figure 2:
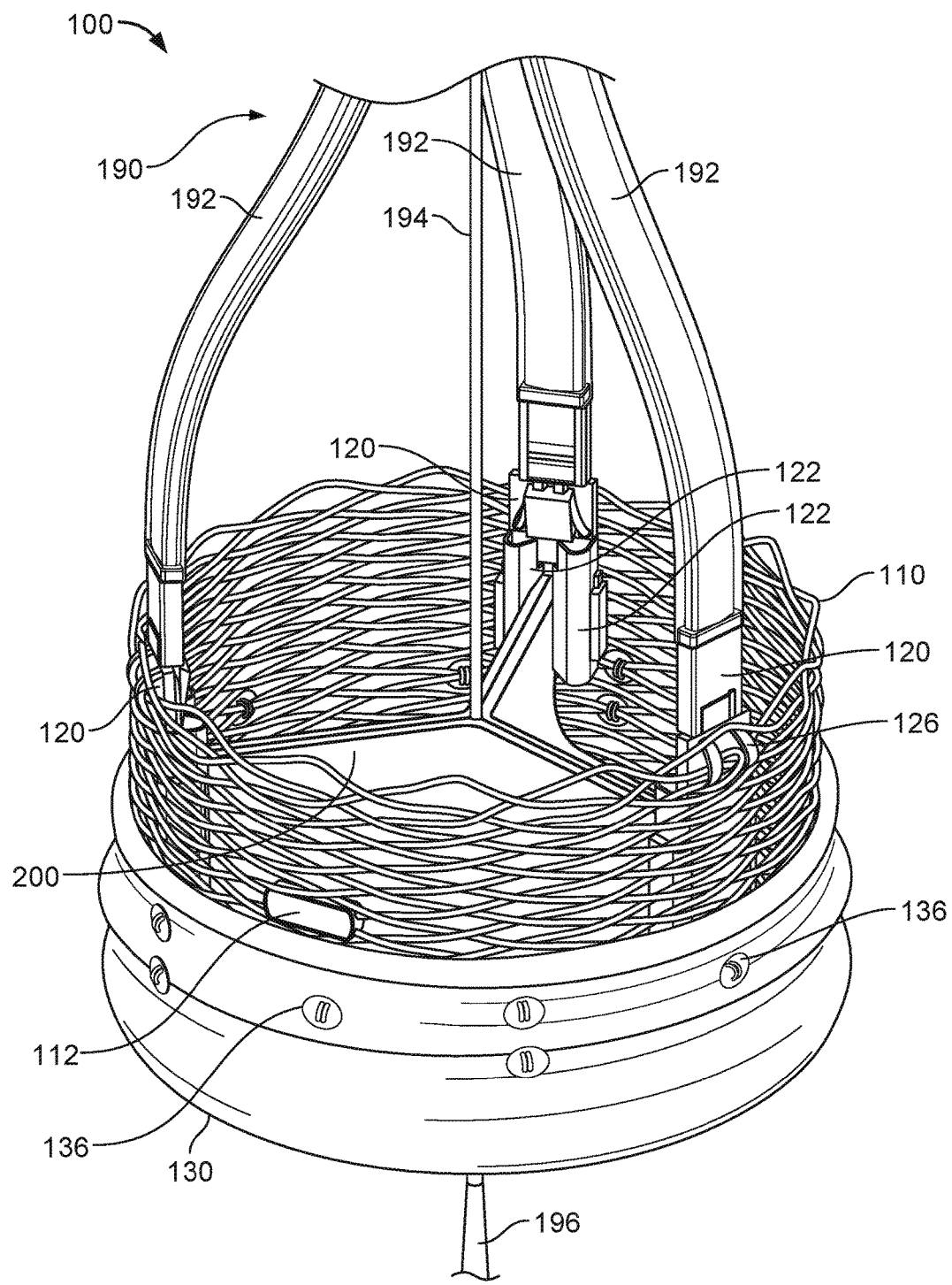
FIG. 2 is an exemplary prosthetic heart valve.

After obtaining biological tissue, such as bovine pericardium 30, the biological tissue can be fixed in step 12, which is described below. In step 13, leaflets having a predetermined shape are cut from the fixed biological tissue, and suitable leaflets are selected for use in a prosthetic heart valve. In step 14, a prosthetic heart valve is fabricated using one or more of the cut leaflets. For example, three leaflets including the biological tissue can be stitched to a frame and/or to each other to form a prosthetic heart valve. An exemplary heart valve is depicted in FIG. 2 and described below. In step 15, prosthetic heart valves can be inspected and/or tested to ensure that they meet specifications. In some cases, a prosthetic heart valve can be sterilized before or after inspection.

An exemplary process of fixing biological tissue 12 is further shown in the flow chart of FIG. 1B. Processes provided herein for tissue modification can use one or more of the steps depicted in FIG. 1B. In step 21, a patch of biological tissue is cut to simplify the tissue modification processes provided in steps 22-26. In some cases, the patch of biological tissue can be substantially rectangular. In some cases, the patch of biological tissue can be cut such that it can be laid in a substantially flat configuration. In some cases, the patch of biological tissue can be cut such that thickness variations are minimized. The particular size and shape of the patch can be dictated by the particular biological tissue being processed. Step 21 can be cut by hand with the aid of a template approximating the shape of the biological tissue, as shown in FIG. 1B. In some cases, step 21 can be automated using opposite male and female mold members and a control system to cut the biological tissue along predetermined lines. Although the biological tissue can be cut in step 21 to minimize variations in mechanical properties of the biological tissue in the patch, natural variations are expected, thus the devices, systems, and methods provided herein can further tension and fix the biological tissue to produce reliable and consistent mechanical properties in the biological tissue. In some cases, the biological tissue can have an initial thickness of about 0.05 mm to about 0.7 mm. In some cases, a biological tissue supply can supply a precut patch of biological tissue thus avoiding the need to perform step 21.

In step 22, the biological tissue is tensioned. For example, a plurality of grippers arranged around a bovine pericardium patch 32 over a frame and stretched to tension patch 32. In step 23, the tensioned patch 32 is captured on the frame to retain the tensioning for further processing. For example, as shown, tensioned patch 32 can be secured on the frame by a plurality of staples 820 to create a tissue-frame assembly 800. In step 24, the tensioned patch 32 is chemically cross-linked to fix the biological tissue. As shown, step 24 can use glutaraldehyde. In some cases, tissue-frame assembly 800 can be placed in a solution including 0.6 wt % glutaraldehyde for at least 15 minutes to chemically cross-link the biological tissue. In some cases, tissue-frame assembly 800 can be placed in a solution of glutaraldehyde for up to 30 days. In some cases, tissue-frame assembly 800 can be placed in a solution of glutaraldehyde for between 30 minutes and 6 hours. In some cases, tissue-frame assembly 800 can be placed in a solution of glutaraldehyde for between 1 hour and 3 hours. In some cases, the solution of glutaraldehyde can have a concentration of glutaraldehyde of between 0.1 wt % glutaraldehyde and 5 wt % glutaraldehyde, between 0.2 wt % glutaraldehyde and 2.0 wt % glutaraldehyde, or between 0.4 wt % glutaraldehyde and 0.8 wt % glutaraldehyde. In some cases, other cross-linking compounds, such as polyepoxides and EDC (carbodiimide), can be used to chemically cross-link the biological tissue on the frame. In some cases, the time under tension (e.g., the time while the tissue is attached to the frame) can be distinct from the amount of time that the tissue is exposed to a cross-linking solution. In some cases, tissue can be separated from the frame and continue to be treated by a cross-linking solution. In some cases, the tissue can remain on a frame for periods of time after the tissue-frame combination is removed from the cross-linking solution and/or remain on the frame for a period of time prior to exposure to the cross-linking solution. In step 25, fixed biological tissue can be separated from the frame. In some cases, the fixed biological tissue can be cut from the fixed and tensioned biological tissue while the fixed and tensioned biological tissue is still secured to the frame. In some cases, the fixed and tensioned biological tissue can be removed from the frame and subsequently cut. In step 26, the fixed and tensioned biological tissue is tested to determine if it meets specifications. For example, a fixed and tensioned biological tissue can have a visual inspection and/or have one or more of the following properties measured: thickness, tension, droop, outer dimensions, shrinkage, water content, and/or weight, to see if the fixed and tensioned biological tissue is suitable for use in a medical device.

FIG. 2 illustrates an exemplary prosthetic heart valve 100 provided herein, which can use leaflets 200 including tensioned and fixed biological tissue provided herein. FIG. 2 is a perspective view of prosthetic heart valve 100 secured to a deployment device 190. As shown, prosthetic heart valve 100 includes an expandable member 110 (e.g., a braided stent), three leaflets 200, three anchor elements 120 that secure sleeve portions 216 of leaflets 200 to expandable member 110, and a tubular seal 130 secured around a blood inflow end of prosthetic heart valve 100. To facilitate better understanding, FIG. 2 does not show components that are located underneath tubular seal 130. Anchor elements 120 can include post leg compression elements 122 and clamping support structures 126 adapted to provide support along opposite sides of the sleeve portions 216. Expandable member 110 shown in FIG. 2 is a braided stent (which can also be described as a braided anchor element), which is adapted to transition between a restricted state having a smaller diameter and an expanded state having a larger diameter. Expandable member 110 can be self-expanding, mechanically expanded, or a combination thereof. In some cases, one or more radiopaque markers can be secured to prosthetic heart valves provided herein. As shown, expandable member 110 includes a radiopaque marker 112. Any suitable radiopaque material (such as platinum, palladium, gold, tantalum, or alloys thereof) can be used as the radiopaque material in radiopaque marker 112. One or more radiopaque markers can be used with an imaging system to help a physician ensure that a valve is set in an appropriate location. In some cases, prosthetic heart valves provided herein include at least three radiopaque markers. Expandable member 110 can have any suitable structure, arrangement, or material. In some cases, expandable member 110 can include a braided wire stent. For example, U.S. Publication Number 2005/0143809, titled, "Methods and Apparatus for Endovascularly Replacing a Heart Valve," and filed on Nov. 5, 2004, which is herein incorporated by reference for its disclosure of possible structures and materials for a braided wire stent, discloses a braided wire stent. In some cases, expandable member 110 includes a shape memory material (e.g., a nickel-titanium alloy or a cobalt-chromium alloy).

In some cases, as shown, prosthetic heart valve 100 includes three leaflets 200. In some cases, prosthetic heart valves provided herein can have any suitable number of leaflets, such as two, three, four, five, or more leaflets. In some cases, leaflets 200 are secured to one another. In some cases, leaflets 200 can be secured to one another by a suture (not shown) or a plurality of sutures. Leaflets 200 can be sutured alongside edges of a body portion of each leaflet. In some cases, prosthetic heart valves provided herein can include a single line of sutures, which can be adapted to minimize leaks, minimize the width of a seam, and/or minimize the profile of a replacement heart valve during a percutaneous insertion. In some cases, prosthetic heart valves provided herein can include multiple lines of sutures.

Referring back to FIG. 1B, step 22, a patch of biological tissue (e.g., bovine pericardium 32) can be tensioned according to methods, devices, or systems provided herein. In some cases, a patch of biological tissue can be tensioned by securing the edges of the patch to a plurality of grippers and applying an equal amount of actuating force to each of the grippers. In some cases, a patch of biological tissue provided herein can be along a single axis for a uniaxial orientation. In some cases, a patch of biological tissue provided herein can be stretched along two axes for a biaxial orientation. In some cases, an amount of force supplied along the two intersecting axes is equal. In some cases, an amount of force supplied along the two intersecting axes is different. In some cases, the axes are perpendicular. In some cases, force is supplied along each axis such that each gripper supplies an equal amount of stretching force to the biological tissue.

Figure 3:
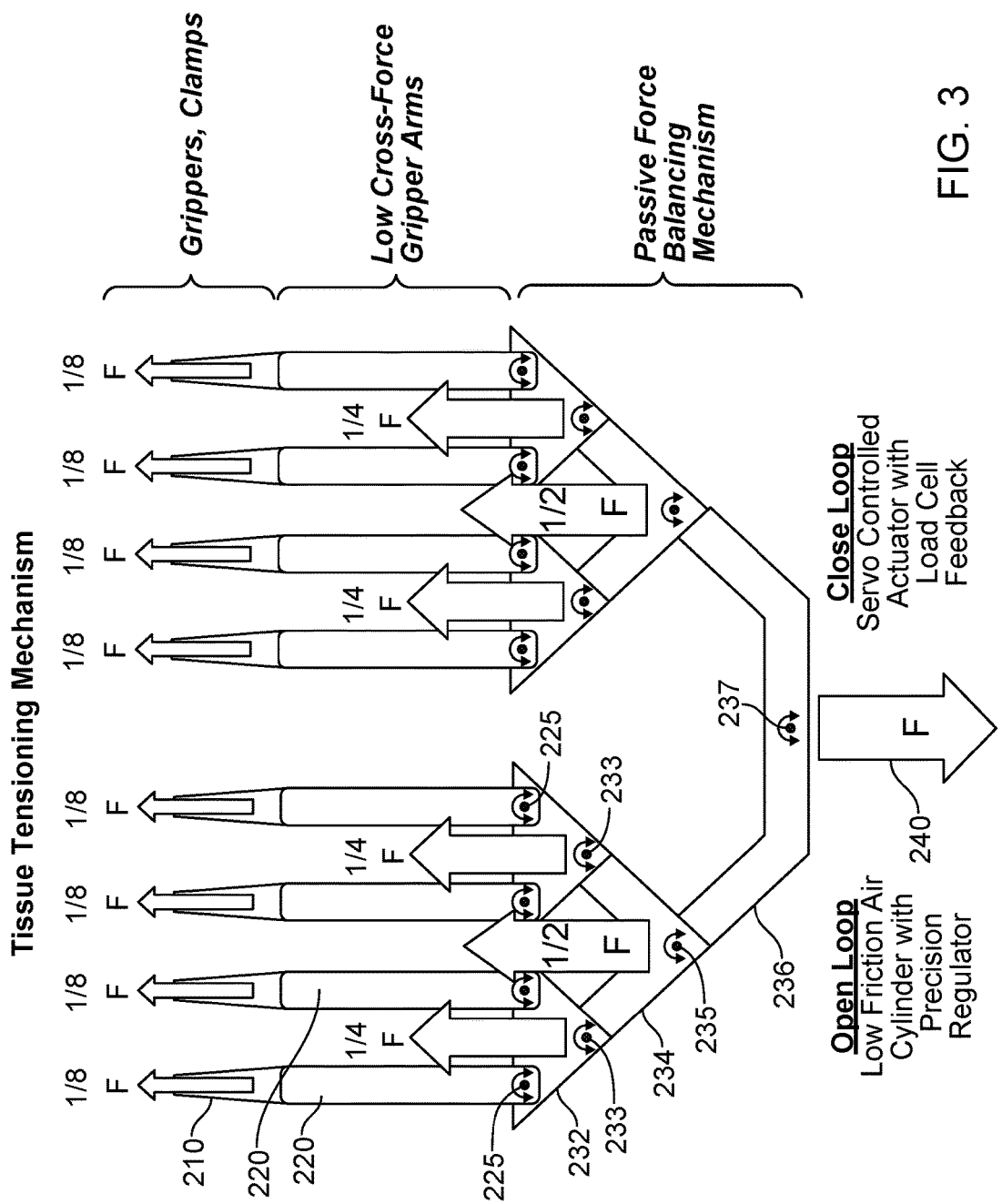
FIG. 3 depicts a schematic depicting how a passive force balancing mechanism divides a force equally between individual grippers.

FIG. 3 depicts a passive force balancing mechanism that can be used in methods, devices, and systems provided herein to provide an equal pulling force to adjacent grippers pulling one edge of a patch of biological tissue. As shown, as single force actuator 240 can be connected to a plurality of grippers 210 via a plurality of pivoted connections 233, 235, 237, 225 to force dividers 232, 234, 236 which each divide an amount of force applied to the grippers in half despite differences in the natural mechanical properties of the biological tissue being stretched/tensioned. Each force divider 232, 234, and 236 has three pivoted connections. Each pivoted connection 233, 235, 237, 225 allows for free rotation about an axis perpendicular to a plane passing through the plurality of grippers 210. The biological tissue can be positioned in the plane.

Force actuator 240 can be any suitable force actuator. In some cases, force actuator 240 can be an open loop force actuator. For example, in some cases, force actuator 240 can be a low friction air cylinder with precision regulator. In some cases, force actuator 240 can be a closed loop force actuator. For example, in some cases, force actuator 240 can be a servo controlled actuator with load cell feedback or moved to a predetermined position/distance. Use of a passive force balancing mechanism provided herein can minimize the number of independently controlled force actuators used to provide force to grippers used to tension/stretch biological tissue.

The plurality of force dividers 232, 234, 236 and pivoted connections 233, 235, 237, 225 allow for the force divided to the grippers 210 to be equally divided, as each force divider 232, 234, 236 divides an amount of force in half. The equal dividing of the force can be due to an equal spacing of the neighboring grippers from the respective pivot points perpendicular to the axis of the grippers (x-axis in FIG. 3). Although shown as having a v-shape, the force dividers can have other shapes, such as triangles or rectangles. Moreover, although the pivot points are depicted as being spread out (in the Y dimension of FIG. 3), the pivot points can also be aligned with each other. If the biological tissue in one area of a biological tissue patch is less elastic than other areas of the patch, the force dividers and beams 220 can pivot about one or more pivoted connections 233, 235, 237, 225 to still supply the desired amount of force to the more elastic regions of the patch. As shown, there are eight grippers 210, but methods, devices, and systems provided herein can use other numbers of grippers. In some cases, grippers supplied to apply force along each axis are equal to a power of two. Some cases, methods, devices, and systems provided herein have 2 grippers, 4 grippers, 8 grippers, 16 grippers, and/or 32 grippers attached to each force actuator 240.

Beams 220 include a distal end secured to a gripper 210 and a proximal end having a pivoted connection 225 to a first force divider 232, which is also pivotally connected to another beam 220 and a second force divider 234. Second force dividers 234 are each pivotally connected to two of the first force dividers 232 and to a third force divider 236. The third force divider is pivotally connected to two of the second force dividers and to force actuator 240. Beams 220 can have a length between pivoted connection 225 and a gripping portion of gripper 210 that is at least 1 cm. In some cases, the length between pivoted connection 225 and a gripping portion of gripper 210 is at least 2 cm. In some cases, the length between pivoted connection 225 and a gripping portion of gripper 210 is at least 2.5 cm. In some cases, the length between pivoted connection 225 and a gripping portion of gripper 210 is between 1.0 cm and 50 cm. In some cases, the length between pivoted connection 225 and a gripping portion of gripper 210 is between 2.0 cm and 10 cm. The length between pivoted connection 225 and a gripping portion of gripper 210 can be sized in order to allow for adjacent grippers 210 to spread with minimum resistance to the grippers being used to stretch the patch along another axis. Allowing the grippers 210 to spread when stretching/tensioning a patch of biological tissue allows for an uneven stretching of the biological tissue in a perpendicular axis. As the beams spread, however, this changes the direction of the force applied to each gripper 210, but longer beams 220 minimize the angle between the vector of force applied by each gripper 210 and the force supplied by the force actuator 240.

Beams 220 can be rigid or flexible. In some cases, beams 220 can be constructed out of a rigid material (e.g., steel, aluminum). In some cases, beams 220 can be constructed of a flexible plastic. In some cases, beams 220 can include flexible cables/tethers adapted to elastically or plastically stretch when subjected to a force exceeding a predetermined force.

Figure 4:
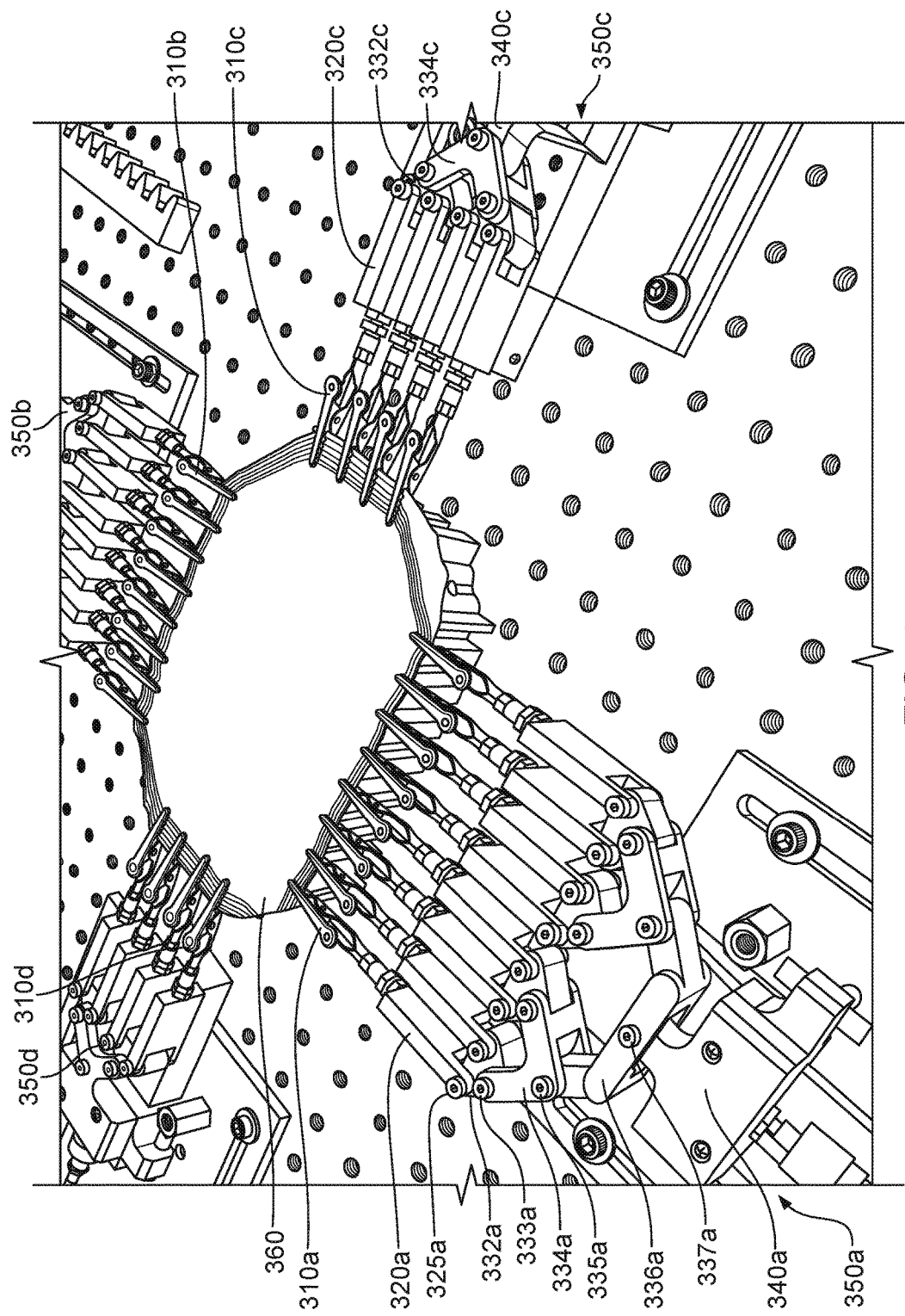
FIG. 4 illustrates an exemplary tissue stretching device.

FIG. 4 depicts an exemplary tissue stretching/tensioning device according to particular embodiments provided herein. As shown, a substantially rectangular patch of biological tissue 32 is secured above a frame 360 by a plurality of grippers 310a, 310b, 310c, 310d. As shown, the grippers 310a, 310b, 310c, and 310d along each edge of the patch 32 are connected to a passive force balancing mechanism 350a, 350b, 350c, 350d. As shown, opposite passive force balancing mechanisms 350a and 350b are each connected to eight grippers 310a, 310b. As shown, opposite passive force balancing mechanisms 350c and 350d are each connected to four grippers 310c, 310d. Force balancing mechanism 350a includes a first force actuator 340a pivotally connected to force divider 336a at pivoted connection 337a. Force divider 336a is pivotally connected to two force dividers 334a at pivoted connections 335a. Each force divider 334a is connected to two force dividers 332a at pivoted connections 333a. Each force divider 332a is connected to two beams 320a at pivoted connections 225a. A distal end of each beam is connected to a gripper 310a. Force balancing mechanism 350b has the same structure as force balancing mechanism 350a connecting a second force actuator to eight grippers 310a. Force balancing mechanism 350c includes a third force actuator 340c pivotally connected to force divider 334c at pivoted connection 335c. Force divider 334c is pivotally connected to two force dividers 332c at pivoted connections 333c. Each force divider 332a is connected to two beams 320c at pivoted connections 225c. A distal end of each beam is connected to a gripper 310c. Force balancing mechanism 350d has the same structure as force balancing mechanism 350c connecting a fourth force actuator to four grippers 310d. As shown, beams 320a, 320c can have a length of at least 1 cm. As shown, the length of beams 320a, 320c can be approximately the width of patch 32. As discussed above, the length of the beams can impact the direction of the force vector applied to each gripper as the beams pivot.

The grippers 310a, 310b, 310c, and 310d can have any suitable structure. In some cases, grippers 310a, 310b, 310c, and 310d can be pneumatic grippers. In some cases, grippers 310a, 310b, 310c, and 310d can be spring loaded serrated clamps (e.g., alligator clips). In some cases, grippers 310a, 310b, 310c, and 310d can include hooks, clamps, magnets, spikes/pins/nails, self-tightening mechanisms, electric grippers, and/or solenoids. The surface texture of a gripper can be designed to prevent material slippage. In some cases, grippers can have a serrated/knurled surface.

Figure 5:
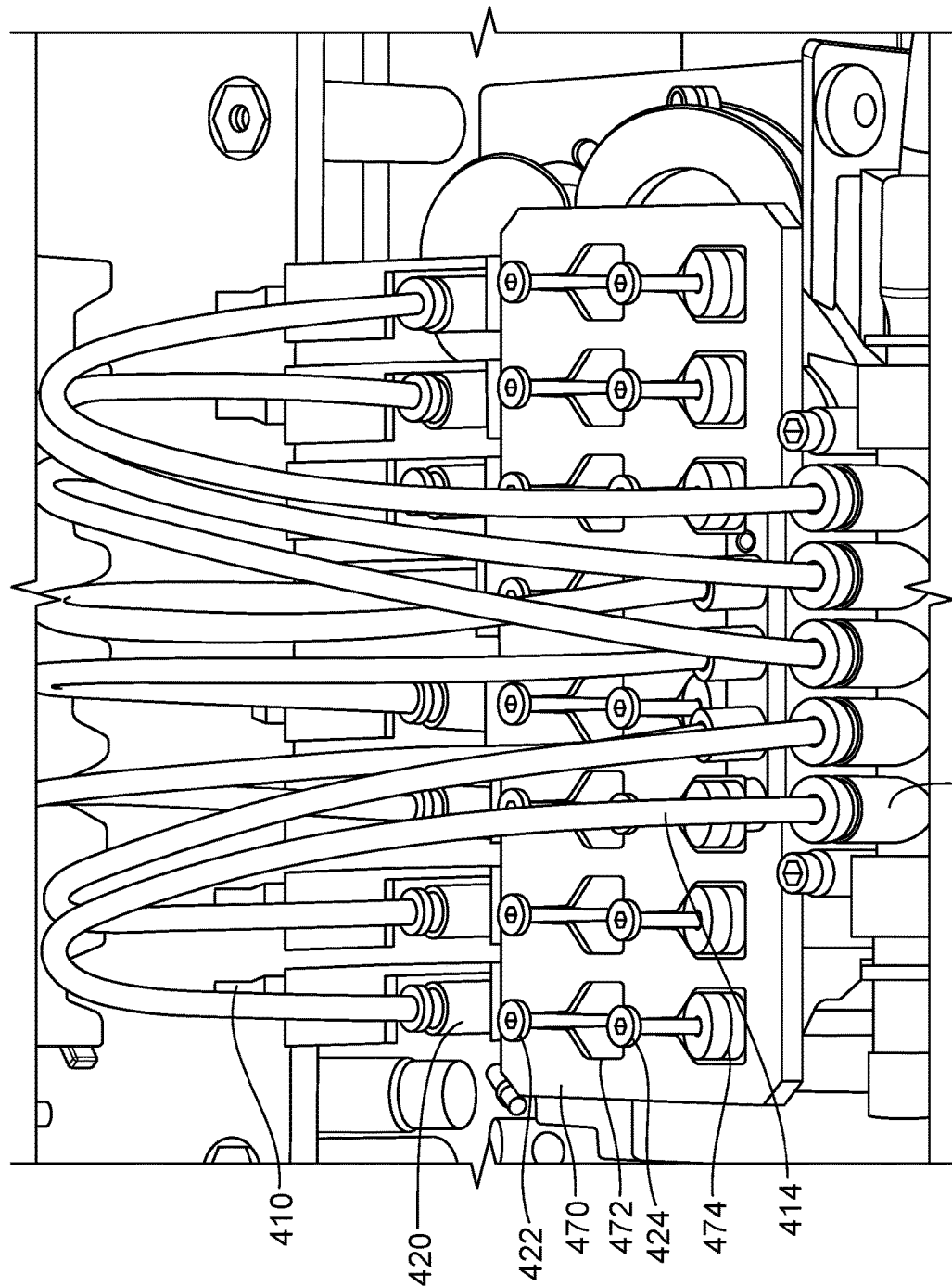
FIG. 5 illustrates an exemplary jig used to lock individual grippers into a predetermined spacing.

To mount patch 32, the patch can be placed over frame 360 and four respective edges of patch 32 can be secured to each of grippers 310a, 310b, 310c, 310d. During the process of securing patch 32 to grippers 310a, 310b, 310c, and 310d the pivoted connections connecting each gripper to a force actuator can be locked so that the spacing between each adjacent gripper along each edge is at a predetermined distance. In some cases, a jig can be used to lock the grippers 310a, 310b, 310c, 310d into a predetermined arrangement. For example, FIG. 5 illustrates an exemplary jig 470 that can include a plurality of apertures 472, 474 that correspond to projections 422, 424 extending from each beam 420. Each aperture 472, 474 includes a pointed end and an open section. In some cases, apertures 472, 474 can have slotted ends. For example, jig 470 can include distal apertures 474 having a slotted end to prevent rotation and the proximal apertures can have pointed ends (v-groove), to set a constant pitch. In order to lock the grippers 410 into a predetermined spacing, jig 470 can be advanced rearward towards the force actuator (not shown) such that each projections 422, 424 are each seated in the pointed end of each aperture 472, 474 so that each beam 420 is aligned along a plane passing through the pointed ends of each pair of apertures 472, 474. To allow the beams 420 to pivot relative to each other, jig 470 is advanced forward such that each projection is free to move within the open section. In some cases, apertures 472, 474 can have a pointed end on the rear side of jig 470 such that the jig can be advanced forward relative to the force actuator to lock the grippers 410 in a predetermined spacing relationship. The jig and its actuator are fixedly coupled to the gripper actuator. Although FIG. 5 depicts a particular embodiment of a jig used to lock the position of grippers 410, other jig arrangements for locking the spacing of grippers relative to each other and/or to the force actuator are also contemplated. For example, a jig including a slotted groove at the edge could be used, which would remove the need for two apertures. FIG. 5 also depicts pneumatic grippers 410 connected to pneumatic tubes 414 connected to an air supply 412.

Figure 6:
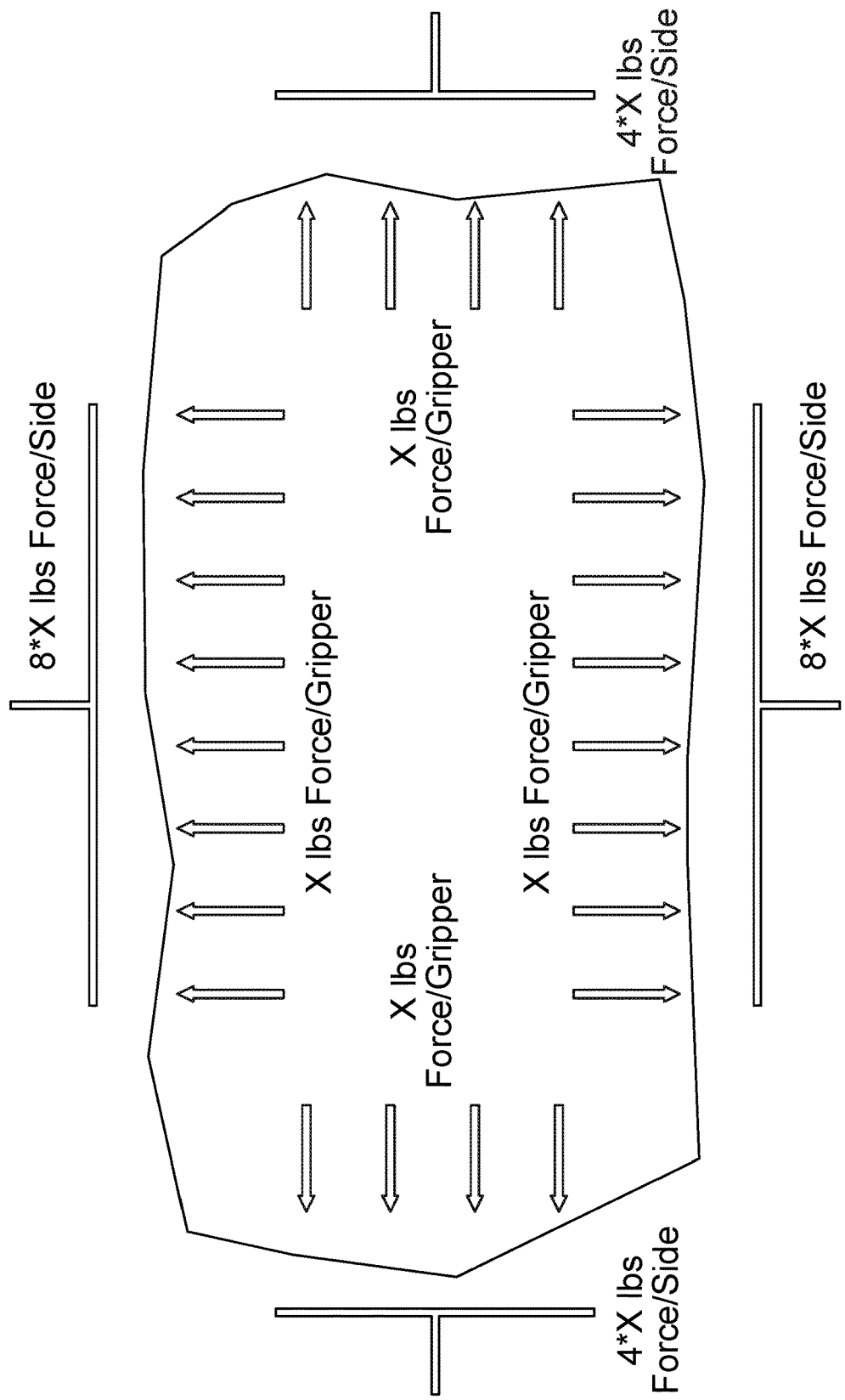
FIG. 6 shows how force can be applied along 4 sides of a patch of tissue so that each individual gripper applies an equal amount of force.

In use, first and second sets of grippers on opposite sides of a patch of biological tissue can have jigs moved to locking positions to fix the spacing of adjacent grippers. Third and fourth sets of grippers, adjacent to the first and second sets of grippers, can also have jigs moved to locking positions to fix the spacing of adjacent grippers. Once the spacing of the grippers is locked, the grippers can be secured to edge portions of a patch of biological tissue. After securing the grippers to the patch, the jigs can be moved into unlocked positions. After the jigs are moved to an unlocked position, each force actuator can apply a predetermined force to stretch the patch. As shown in FIG. 6, the force applied by each force actuator can be adapted such that each gripper applies the same amount of force, X lbs force, to each gripper. For example, in the case where first and second sets of grippers each include eight grippers and third and fourth sets of grippers each include four grippers, the force applied by first and second force actuators can be 8 times X lbs of force and the force applied by third and fourth force actuators can be 4 times X lbs of force so that each gripper pulls with X lbs of force. In some cases, each gripper stretches the patch with at least 0.01 lbs force. In some cases, each gripper stretches the patch with a force between 0.01 lbs force and 5 lbs force. In some cases, each gripper stretches the patch with a force between 0.05 lbs force and 3 lbs force. In some cases, each gripper stretches the patch with a force between 0.1 lbs force and 1 lb force. In some cases, each gripper stretches the patch with a force between 0.2 lbs force and 0.5 lbs force. In some cases, the force actuator can be servo controlled with load cell feedback, which can allow for a lower forces to be supplied. As the force actuators apply force to the grippers, natural variations in the mechanical properties of the patch of biological tissue can result in relative movement of adjacent grippers in each set such that force is equalized between the grippers in each set. The relative movement of the first and second sets of grippers away from one another along a first axis and the relative movement of the third and fourth sets of grippers away from one another along a second axis perpendicular to the first axis results in the application of a biaxial stress load to the patch of biological tissue (e.g., the tissue 32).

As used herein, "stress load" is the force (measured, e.g., in lbs force) applied to the tissue. As used herein, "stress" is the force (i.e., stress load) per unit area of the tissue and can be measured, for example, in lbs force per square inch. Accordingly, the stress applied to the tissue is a function of the stress load and the cross-sectional area of the tissue. For example, for a given stress load, the stress applied to the tissue may vary with the thickness of the tissue.

Figure 7:
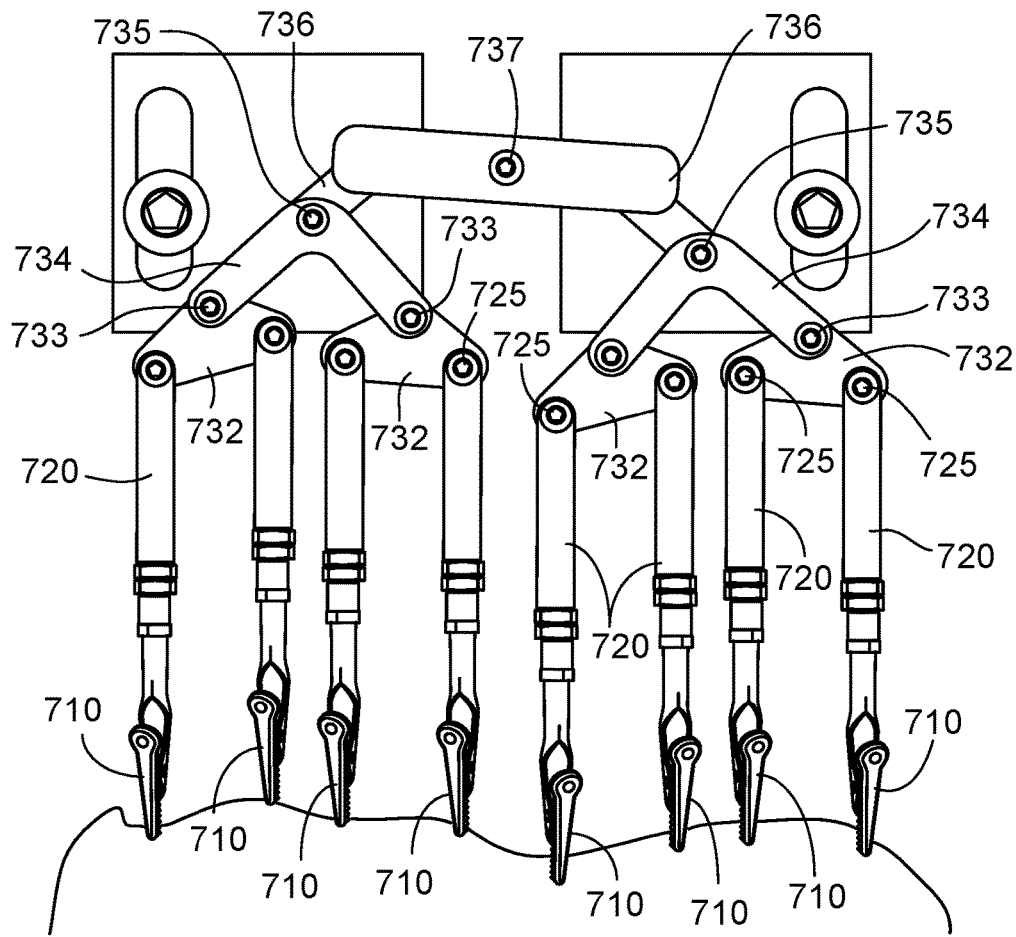
FIG. 7 depicts how the passive force balancing mechanism can dynamically adjust for tissue with uneven elastic properties.

FIG. 7 illustrates how the pivoting connection can improve tensioning of biological tissues having natural variations in properties. As shown, FIG. 7 does not maintain the alignment and spacing of adjacent grippers, and thus there is variable stretching of different regions of the tissue.

Figure 8:
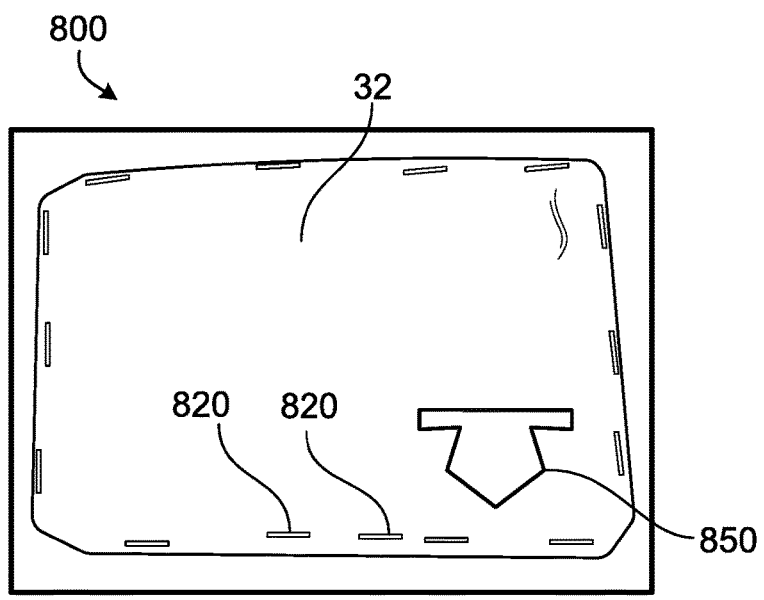
FIG. 8 depicts how the leaflets are cut out of the stretched and treated patch of tissue.
Figure 9:
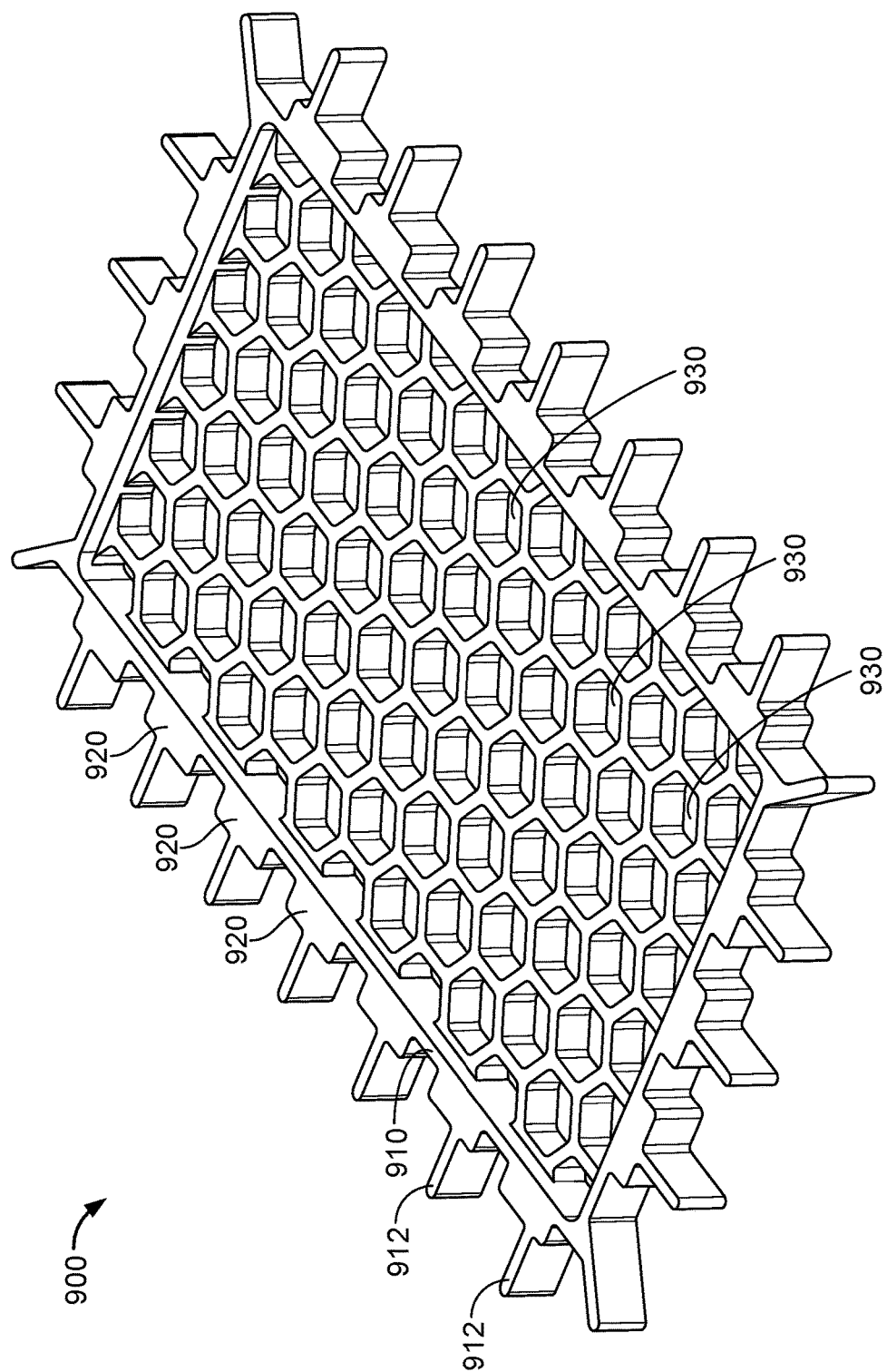
FIG. 9 depicts an exemplary fame.

In some cases, the first, second, third, and fourth sets of grippers can be simultaneously actuated to stretch biological tissue. In some cases, first and second sets of grippers are actuated to stretch the tissue along a first axis followed by the third and fourth sets of grippers being actuated to stretch the tissue along a second axis. In some cases, the tissue can enter a precycle where loads are applied to the tissue patch in one or more cycles to tension it at least one time prior to the final tension. In some cases, the stress loads applied along each axis is about 0.1 N to about 2 N. In some cases, the stress applied to the patch is about 0.01 N/mm2 to about 2 N/mm2. As discussed above in relation to FIG. 1B, after the patch of biological tissue is stretched to the desired tension, the tissue can be secured to a frame in step 23. As shown in FIG. 8 and FIG. 1B, staples 820 can be used to secure patch 32 to a frame to produce a frame-tissue combination 800, which keeps patch 32 in a tensioned configuration such that it does not recoil. An exemplary frame is shown in FIG. 9. As shown in FIG. 9, frame 900 includes a rim 910 including a plurality of thickened sections 920 adapted to receive staples 820. Frame 900 can include a series of projections 912. Projections 912 can act as a shelf to suspend the tissue in the plane of the grippers to allow the grippers to straddle the tissue without interference upon approach. In some cases, not shown, the frame can be hollow. In some cases, frame 900 can include reinforcing structures adapted to prevent rim 910 from warping when stapled to rim 910. In some cases, a plurality of apertures 930 can ensure that both the upper and the lower surface of the patch of tissue are treated in subsequent treatment steps discussed below, such as the chemical cross-linking of the patch of biological tissue. Other frame arrangements can also be used.

Frame 900, or other frame designs, can be made out of any suitable material. In some cases, frame 900 is made out of plastic. In some cases, frame 900 is made out of a metallic material. In some cases, frame 900 can be medical grade or food grade plastics or corrosion resistant stainless steel or other materials suitable for use in a corrosive environment while still permitting cleaning.

Any suitable fastening means can be used to secure the tensioned patch of biological tissue to a frame. Although staples are depicted, other fasteners are also contemplated. For example, in some cases, clamps can be used to secure the tensioned patch of biological tissue to the frame. Other fasteners available for use in systems and methods provided herein include sutures, spikes, magnets, tethers, pins, nails, screws, clamps, and/or tortuous pathways. After the tensioned patch of biological tissue is secured to a frame, the biological tissue can be cut from the grippers by cutting around the perimeter of the frame or released from the grippers.

In some cases, a frame can be used along with a platens to flatten tissue to provide a more consistent thickness prior to fixation. A bottom plate can be sized to fit within the tissue fixation frame, and a top platen can be expanded to include a flat rectangular plate of the same size as the bottom platen. The top platen can be program controlled so that it will compress to a fixed thickness. Alternatively spacers can be used to limit the travel of the moveable platen using a mechanical method. Both achieve the same result, to limit the amount of travel of the movable platen to a fixed distance, thereby providing tissue of a fixed thickness. In some cases, the bottom platen could be the movable platen with the top platen fixed. The flattening process could occur at a separate station, as shown above, or be integrated into a tissue modification device provided herein. Platen materials can be medical grade or food grade plastics or corrosion resistant stainless steel or other materials suitable for use in a corrosive environment while still permitting cleaning. In some cases, a highly polished and smooth stainless steel can be used as the platen surface to resist any transfer/imprinting of features (e.g., mold lines, machine lines, etc.) from the platen to the tissue.

In step 24 discussed above in relation to FIG. 1B discusses the fixation of the tissue by treating the tensioned tissue with a chemical to cross-link the biological material. In some cases, tissue-frame combination 800 is chemically treated for at least 5 minutes. In some cases, tissue-frame combination 800 is chemically treated emersion into a glutaraldehyde solution for between 5 minutes and 1 week. In some cases, tissue-frame combination 800 is chemically treated emersion into a glutaraldehyde solution for between 10 minutes and 6 hours. In some cases, tissue-frame combination 800 is chemically treated emersion into a glutaraldehyde solution for between 20 minutes and 2 hours. In some cases, tissue-frame combination 800 is chemically treated emersion into a glutaraldehyde solution for between 30 minutes and 1 hour. Additionally or alternatively, tissue-frame combination 800 can be exposed to a non-cross linking-solution (e.g., phosphate-buffered saline or saline) prior to exposure to a glutaraldehyde solution. The exposure of tissue-frame combination 800 to the non-cross linking solution could be carried out between about 4° C. to about 37° C. (e.g., about 20° C.). The exposure of tissue-frame combination 800 can allow the tissue to respond to the stress and reorient prior to locking that structure in place with a cross-linking solution, such as glutaraldehyde.

In some cases, the stretching and fixing of the patch of biological tissue can reduce the average thickness. For example, the average thickness of the tensioned and fixed tissue held in the frame can be about 0.1 mm to about 0.4 mm. In some cases, biaxial stretching of tissue and fixing the tissue results in little to no increase in thickness in the tissue.

A number of embodiments of the invention have been described. Nevertheless, it will be understood that various modifications may be made without departing from the spirit and scope of the invention. Accordingly, other embodiments are within the scope of the following claims.

What is claimed is:

1. A tissue modification apparatus comprising:
a first plurality of grippers aligned in a plane adapted to secure a first edge of a patch of tissue within the plane;
a first plurality of force dividers aligned in the plane with the first plurality of grippers;
wherein the first plurality of grippers are connected to a first force actuator via a plurality of pivoted connections to the first plurality of force dividers, the first plurality of grippers and the first plurality of force dividers are adapted to pivot about an axis perpendicular to the plane.

2. The tissue modification apparatus of claim 1, further comprising a second plurality of grippers aligned in the plane opposite the first plurality of grippers, the second plurality of grippers being adapted to secure a second edge of a patch of tissue, the second plurality of grippers each being adapted to pivot about an axis perpendicular to the plane, the first plurality of grippers being adapted to pull the tissue in a direction opposite the second plurality of grippers such that a patch of tissue secured between the first and second plurality of grippers can be stretched along a first orientation.

3. The tissue modification apparatus of claim 2, wherein the second plurality of grippers are each secured to a second force actuator via pivoted connections such that the first and second force actuators are adapted to pull the first and second pluralities of grippers in opposite directions such that a patch of tissue secured between the first and second plurality of grippers can be stretched along a first orientation.

4. The tissue modification apparatus of claim 2, wherein the second plurality of grippers are attached to a stationary object via pivoted connections.

5. The tissue modification apparatus of claim 2, further comprising a third plurality of grippers and a fourth plurality of grippers, the third plurality of grippers being aligned in the plane adjacent the first plurality of grippers and the fourth plurality of grippers being aligned in the plane opposite the third plurality of grippers, the third and fourth pluralities of grippers each being adapted to secure a third and fourth edge of a patch of tissue, wherein at least the third plurality of grippers are each secured to a third force actuator adapted to pull the third plurality of grippers in a direction opposite the fourth plurality of grippers such that a patch of tissue secured between the first, second, third, and fourth plurality of grippers can be stretched along both the first orientation and a second orientation.

6. The tissue modification apparatus of claim 5, further comprising a fourth force actuator and the third and fourth force actuators are adapted to pull the third and fourth pluralities of grippers in opposite directions.

7. The tissue modification apparatus of claim 5, wherein each of the grippers in the third and fourth pluralities of grippers are adapted to pivot in the plane via a plurality of pivoted connections.

8. The tissue modification apparatus of claim 1, wherein each of the grippers is secured to a distal end of a beam, each beam being pivotally connected to one of the first plurality of force dividers.

9. The tissue modification apparatus of claim 8, wherein each force divider is pivotally connected to either another force divider or to one of said force actuators and each force divider includes at least three pivoted connections.

10. The tissue modification apparatus of claim 8, further comprising a beam fixation device adapted to lock grippers in one of said pluralities of grippers into a predetermined spacing, the beam fixation device being adapted to be released to allow for the grippers to pivot after being secured to an edge of tissue.

11. The tissue modification apparatus of claim 8, wherein each beam is at least 1 cm long.

* * * * *